US006593489B1

(12) United States Patent
Smith et al.

(10) Patent No.: US 6,593,489 B1
(45) Date of Patent: Jul. 15, 2003

(54) SUBSTITUTED CYCLOPENTENES, THEIR PREPARATION AND THEIR USE FOR CHIRAL SCAFFOLDS

(75) Inventors: Mark Edward Brennan Smith, Cambridge (GB); Nadine Derrien, Cambridge (GB)

(73) Assignee: ChirotechTechnology Limited, Cambridge (GB)

( * ) Notice: Subject to any disclaimer, the term of this patent is extended or adjusted under 35 U.S.C. 154(b) by 0 days.

(21) Appl. No.: 09/659,482

(22) Filed: Sep. 11, 2000

(30) Foreign Application Priority Data

Sep. 9, 1999 (GB) ............................................. 9921357
Oct. 8, 1999 (GB) ............................................. 9923953
Dec. 6, 1999 (GB) ............................................. 9928794

(51) Int. Cl.$^7$ ............................................. C07C 69/74
(52) U.S. Cl. ........................ 560/122; 562/504; 548/221
(58) Field of Search ........................ 560/122; 562/504; 548/221

(56) References Cited

FOREIGN PATENT DOCUMENTS

WO            9905144          7/1998

OTHER PUBLICATIONS

Crabtree, Robert H. and Mark W. Davis (1986) "Directing Efects in Homogeneous Hydrogenation with [Ir(cod)(PCy$_3$)(py)]PF$_6$." *J. Org. Chem.* 51:2655–2661.
Stork, Gilbert and Daniel E. Kahne (1983) "Stereocontrol in Homogeneous Catalytic Hydrogenation via Hydroxyl Group Coordination" *J. Am. Chem. Soc.* 105(4):1072–1073.
Hoveyda, Amir H. (1993) "Substrate–Directable Chemical Reactions" *Chem. Rev.* 93(4):1307–1370.
Allan, Robin D., Helena W. Dickenson and Joyce Fong (1986) "Structure–Activity Studies On The Activity Of A Series Of Cyclopentane Gaba Analogues On Gaba$_A$ Receptors And Gaba Uptake" *European Journal of Pharmacology* 122:339–348.
Taylor, Stephen J., Raymond McCague, Richard Wisdom et al.(1993) "Development of the Biocatalystic Resolution of 2–azabicyclo[2.2.1]hept–5–en–3–one as an entry to Single–Enantiomer Carbocyclic Nucleosides" *Tetrahedron Asymmetry* 4(6):1117–1128.
Qiu, Jian, Richard B. Silverman (2000) "A New Class of Conformationally Rigid Analogues of 4–Amino–5–halopentanoic Acids, Potent Inactivators of γ–Aminobutyric Acid Aminotransferase" *J. Med. Chem.* 43:706–720.
Adger, Brian, Ulrich Berens, Matthew J. Griffiths et al. (1997) "Chemoenzymatic synthesis of a novel ligand for rhodium–catalysed asymmetric hydrogenation" *Chem. Commun.*, pp. 713–714.

Takagi, Masatoshi and Keiji Yamamoto (1991) "Carbamate–Directed Stereoselective Hydrogenation and Kinetic Resolution of N–Protected α–(α–Aminoalkyl)acrylates" *Tetrahedron* 47(42):8869–8882.
Cermak, Richard C. and Robert Vince (1981) *Tetrahedron Letters* 22(25):2331–2332.
Chemical Abstracts, Columbus, OH, US, vol. 116(3), (Jan. 20, 1992).
Brown, John M., Alun P. James and Louise M. Prior (1987) "Kinetic Resolution in the Directed Hydrogenation of N–Substituted α–(Aminoalkyl) Acrylates, Precursors of Optically Active β–Amino Acids" *Tetrahedron Letters* 28(19):2179–2182.
Palmer, Christopher F., Keith P. Parry and Stanley M. Roberts (1991) "Electrophilic Substitution of a 2–Azabicyclo[2.2.1]hept–5–en–3–one as a Potential Route to 3–Deoxycarbocyclic Nucleosides" *J. Chem. Soc. Perkin Trans.*

*Primary Examiner*—Paul J. Killos

(57) ABSTRACT

3,4-Disubstituted-1-cyclopentene compounds, in substantially enantiopure form, have the relative stereochemistry according to formula (1A) or (1B)

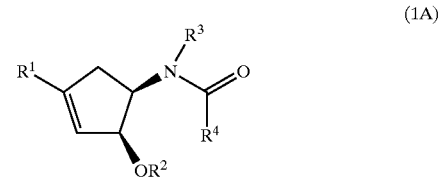

(1A)

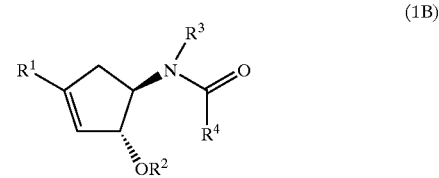

(1B)

including the opposite enantiomers thereof, wherein $R^1$ is either
  COOX, wherein X is selected from the group consisting of alkyl, H, and a salt-forming cation, or
  CH$_2$OH, whererin the hydroxy group is optionally protected;
$R^2$ is H or a protecting group;
$R^3$ is H or alkyl, and
$R^4$ is selected from the group consisting of H, alkoxy, alkyl, aryl, and aralkyl; or, in the case of formula (1A), $R^2$ and $R^4$ are linked to form an oxazolidonone ring.

These compounds can be used to prepare a series of complementary stereochemcially varied cyclopentane scaffolds.

31 Claims, No Drawings

SUBSTITUTED CYCLOPENTENES, THEIR PREPARATION AND THEIR USE FOR CHIRAL SCAFFOLDS

FIELD OF THE INVENTION

This invention relates to novel substituted cyclopentenes and their use, e.g. via directed hydrogenation, in the synthesis of chiral scaffolds for the preparation of information-rich single enantiomer compound libraries.

BACKGROUND OF THE INVENTION

The use of combinational chemistry to synthesize libraries of compounds for screening of biological activity is now a central part of the drug discovery process. Compound diversity is widely perceived to be crucial in order to maximize the information gathered and the probability of finding a lead, and to this end there is an increasing requirements for novel and structurally diverse libraries. One element of diversity can be a variation of the stereochemistry in a scaffold from which the library is formed.

Whilst library diversity is a major consideration, it has to be considered together with other factors such as ease of synthesis, molecular size, lipophilicity, rigidity, solubility and pharmacophore focus. Pharmacophore scaffolds for library generation to data are of limited availability, and tend to be flat and thus two-dimensional. There is a need for more three-dimensional chiral building blocks, which are small and contain multiple points of functional attachment, and which have some resemblance to a known pharmacophore.

In a typical drug discovery process, the first stage of lead identification is to screen a library widely, including mixtures of isomers. Having done this, any hits are defined and deconvoluted into their component-contributing features and further optimised. It is at this relatively late stage that isomer formation is considered, and the medicinal chemist is challenged with synthesizing the separate isomers and testing individually for activity and selectivity. Screening isomer mixtures can also lead to false positives, since an isomer mixture in which any component is active will give an active mixture. However, and importantly, if any component is unselective the mixture will be unselective. This means that an active but unselective mixture may contain a valuable selective component.

A more efficient strategy for drug discovery is to begin screening using a library whose individual compounds are single isomers, thus incorporating a lead characterisation stage into the initial lead identification. This generates more 3-dimensional information that can be enhanced further by applying computational methods for lead optimisation. In order to prepare single isomer libraries, there is a requirement for the appropriate chiral scaffolds in isometrically pure form, in which relative and absolute configurations are defined across all stereogenic centres. It is equally important that, for a scaffold having a particular bond connectivity, all possible stereoisomers can be prepared. Thus a series of scaffolds of this type can be elaborated chemically into different but defined directions of 3-D space, to give isomeric compounds which may have very different properties in a chiral biological environment. In summary, differing stereochemistry at the points of attachment to a scaffold molecule provides a compound library having enhanced information. For an overview of this strategy, see McCague, *Modern Drug Discovery,* Jul./Aug. 29, 2000, (published after the priority dates claimed herein).

In the preparation of organic compounds that contain two or more stereogenic centres, a common synthetic strategy is to utilise a functional group, attached to a pre-existing stereogenic centre in the substrate, as a stereochemical control element for the creation of new stereogenic centres. Processes of this type are frequently referred to as substrate-directable chemical reactions (for a review, see Hoveyda et al, *Chem. Rev.,* 1993, 93, 1307). Although primarily a means of controlling relative configuration of products, this approach has particular value in applications where the substrate is readily accessible in enantiomerically pure form.

Successful implementation of a substrate-directable reaction requires a transient bonding interaction between the direction functional group and either the reagent or a catalyst. This contrast with, and is frequently complementary to, reactions where stereoselectivity is achieved through steric efforts alone, in which no such interaction occurs. In addition, conformational effects in the substrate can influence the relative orientation of the directing group and the reaction site, and different effects may prevail in small- and medium-ring cyclic substrates compared with acyclic and large-ring cyclic substrates.

One category of substrate-directable reactions is directed homogenous hydrogenation. It is well established that, in the presence of a catalyst comprising a transition metal-phosphine complex, hydrogen may be efficiently transferred from the metallic centre to unsaturated organic molecules under homogenous conditions. The reactivity of the intermediate transition metal hydrides depends on both the metal and the electronic and steric properties of the ligands. Metals have proven useful in achieving such transformations include rhodium, iridium and ruthenium, and a variety of phosphines, both chiral and achiral, have received attention as suitable ligands. Such hydrogenations can be made stereoselective by utilizing functional groups present in the substrate to chelate to the catalyst, although a practice, only a limited number of functional groups are well characterized as being capable of directing the hydrogenation efficiently.

For example, studies by Stork and Kahne (*J. Am. Chem. Soc.,* 1983, 105, 1072) and independently by Crabtree and Davis (*J. Org. Chem.,* 1986, 51, 2655) have shown that the hydroxyl group, in conjunction with $[Ir(COD)py(PCy_3)]PF_6$ as catalyst, is highly effective as directing group in the hydrogenation of cyclic alkenes. Stereocontrol was highest in cases where the hydroxyl group is attached directly to the cycloalkene ring, although an acceptable level of stereocontrol was also achieved in cases where an intervening methylene unit is present. Comparative experiments on O-acetyl derivatives (Stork and Kahne), in which no stereocontrol was observed, underline the effectiveness of hydroxyl as a directing group.

Amides and esters, in which the carbonyl group is either attached directly or linked via a methylene unit to a cycloalkene ring, and also ethers, act as efficient directing groups in hydrogenations catalysed by $[Ir(COD)py(PCy_3)]PF_6$. For these substrates and hydroxyl-containing substrates, comparable selectivity can also be achieved using certain rhodium complexes as catalysts, for example the cationic complex $\{Rh[nbd][Ph_2P-(CH_2)_4-PPh_2]\}BF_4$ (for lead references, see pp. 1331–1336 in Hoveyda et al, supra).

Amines, or simple protected derivatives thereof, have been reported as useful directing groups only in isolated examples, for acyclic allylic substrates (Brown et al., *Tetrahedron Lett.,* 1987, 28, 2179; Takagi and Yamamoto, *Terrahedron,* 1991, 47, 8869).

Carbocyclic nucleoside drugs having potent antiviral properties can be synthesised using enantiometrically pure (−)-2-azabicyclo[2.2.1]hept-5en-3-one as a chiral building block. An economical bioresolution of 2-azabicyclo[2.2.1]hept-5-en-3-one, providing the chiral building block as a single enantiomer, is disclosed in WO-A-98/10075. This bioresolution uses a cloned lactamase at high volume efficiency, and can be operated on a multi-tone scale.

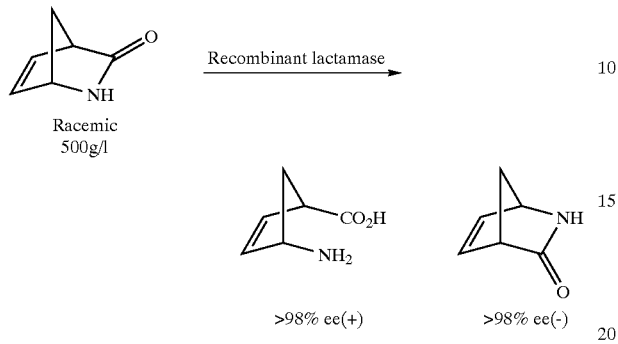

The residual (−)-lactam and the (+)-amino acid product can be converted, using standard chemical methods, into the following single enantiomer N-Boc cis-amino esters

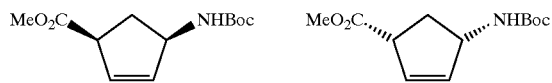

Vince et al, Nucleic Acid Chem., 1991, 4, 46, discloses (3α,4β)-4-amino-3-hydroxy-1-cyclopentene-2-carboxylate.

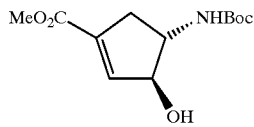

as an intermediate for the synthesis of carbocyclic nucleosides. This compound is in trans configuration, and is a racemate.

An object behind the present invention is the generation of a series of scaffolds comprising the eight trifunctionalised cyclopentanes (a)–(h).

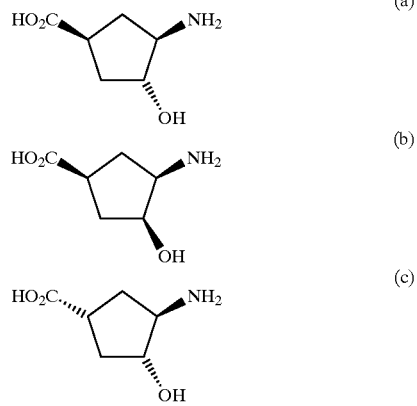

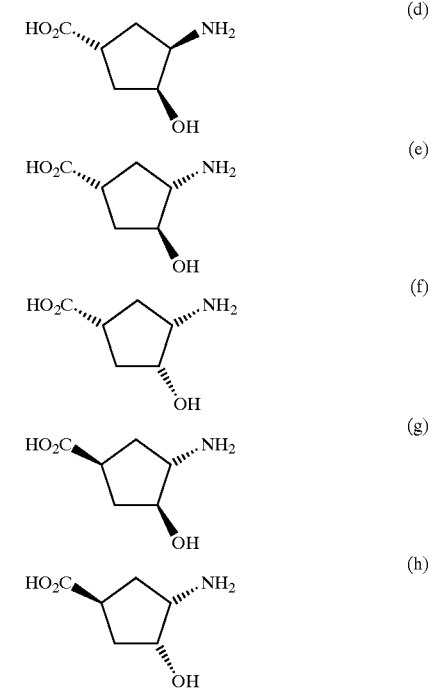

Such compounds can, for example, be considered as precursors to carbocyclic nucleosides, a well-known class of biologically active molecule, or as amino alcohol or amino acid pharmacophores. With appropriate protecting groups, compounds (a)–(h) are ideally suited for further derivatisation in combination fashion. See McCague, supra.

SUMMARY OF THE INVENTION

It is now been appreciated that single enantiomers of 2-azabicyclo[2.2.1]hept-5-en-3-one and the derived cis-amino esters shown above might be convenient intermediates for the preparation of scaffolds (a)–(h), and suitable process chemistry, having the potential for scale-up, has been found. Thus, in the event that screens of a library based on the scaffolds generate useful lead compounds, the appropriate scaffold can be produced in sufficient quantity to support any subsequent drug discovery and development.

One aspect of the present invention is based on the discovery of novel and versatile synthetic intermediates, in substantially enantiopure form, represented by formulae (1A) and (1B)

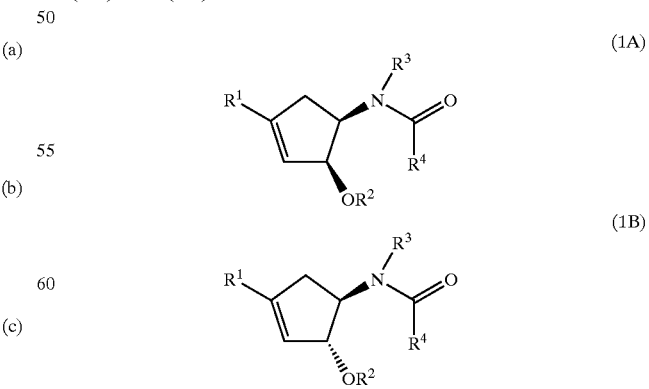

These formulae are to be understood, for the purpose of this specification, to include the respective opposite enantiomers thereof. From these compounds, all eight stereoisomers (a)–(h) of 3-amino-4-hydroxy-1-cyclopentanecarboxylic acid may be prepared stereoselectively, in conveniently protected form.

In a cyclopentene of formula (1), in which the relative stereochemistry of oxygen and nitrogen substituents is cis (1A) or trans (1B), $R^1$ is either COOX, wherein X is alkyl, H or a salt-forming cation, or $CH_2OH$, wherein the hydroxyl group is optionally protected; $R^2$ is H or a protecting group; $R^3$ is H or alkyl; and $R^4$ is H, alkoxy, alkyl, aryl or aralkyl. Optionally, in formula (1A), $R^2$ and $R^4$ are linked to form an oxazolidinone ring, as shown in formula 2

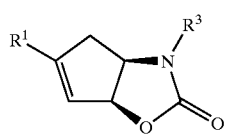

(2)

Compounds of formula (2) are conveniently prepared from an N-Boc cis-4-amino-2-cyclopentene-1-carboxylic ester of formula (3)

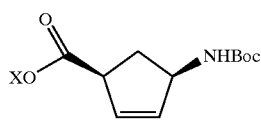

(3)

As indicated above, the starting material (3) is readily obtained in enantiomerically pure form via bioresolution of 2-azabicyclo[2.2.1]hept-5-en-3one.

Another aspect of the present invention is the recognition that a compound of formula (1) can be used to prepare, by way of example, any one of the diastereomerically pure compounds represented by partial structures (4a)–(4d)

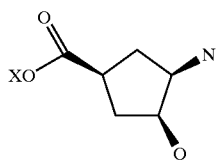

(4b)

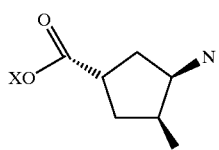

(4d)

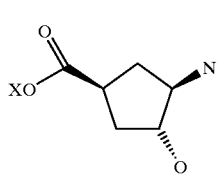

(4a)

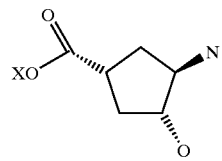

(4c)

and the opposite enantiomers thereof.

A further aspect of a present invention is based on the discovery of conditions that allow the highly stereoselective hydrogenation of cyclic alkenes, directed by an amine group protected as a carbamate derivative. In this reaction, a cycloalkane of formula (5) is prepared from a cycloalkene of formula (6)

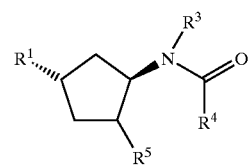

(5)

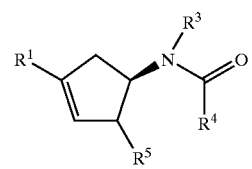

(6)

wherein $R^1$, $R^3$ and $R^4$ are as defined above, and $R^5$ is H, $\alpha$-$OR^2$ or $\beta$-$OR^2$; when $R^5$ is $OR^2$, then formula (6) is the same as (1a) or (1b). This reaction may be conducted in the presence of, as catalyst, a transitional metal-ligand complex, of the type exemplified by the cationic rhodium complexes of bisphospholane ligands of formulae (8) and (9)

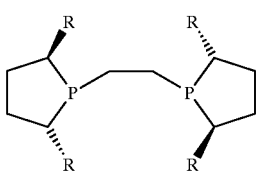

(8)

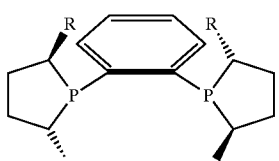

(9)

wherein R is alkyl, each possessing a 2-carbon bridge between the P atoms. More generally, the process of the present invention a means of controlling relative stereochemistry in the creation of new stereogenic centres in the product (5), and for this purpose the starting material (6) may be chiral or achiral. Preferably (6) is chiral and more preferably is a substantially single enantiomer. A substantially single enantiomer of the invention is preferably in an enantiomeric excess of at least 90%, more preferably at least 95% and more preferably at least 98%.

DESCRIPTION OF THE INVENTION

In general terms, the nature of each of the various R groups is not critical. Thus, X may provide an acid, salt or ester; $R^2$ is H or any removable protecting group; $R^3$ is H or alkyl, e.g. methyl or a group of up to, say, 10 or 20 C atoms; and $R^4$ may form an ester or amide, e.g. having up to 10 to 20 C atoms, or, in combinations with $R^2$, a carbamate.

Certain compounds of the invention are preferred. For example, it is preferred that $R^1$ is COOX. X is preferably alkyl. $R^2$ and $R^3$ are each preferably H. $R^4$ is preferably alkoxy. It is particularly preferred that X is methyl or ethyl and $R^4$ is tert-butoxy or benzyloxy. More generally, groups within the scope of the present invention (such as suitable protecting groups) will be apparent to those of ordinary skill in the art.

The preparation of compounds of the invention, and processes of the invention, will now be described by way of example with reference to particular compounds, e.g. in which $R^1$ is COOCH$_3$. It will be understood that these processes can be used when X has other values, or that such compounds can be interconverted. Further, such compounds can be reduced, to give compounds of the invention in which $R^1$ is CH$_2$OH, by conventional methodology, and protected if necessary or desired.

A typical synthesis of compounds of formula (1A), e.g. the specific compound (1C), is illustrated in the following Scheme 1. Here, as in other specific description relating to the invention, there is scope for using alternative reagents in individual steps, which will be recognised by a skilled practitioner.

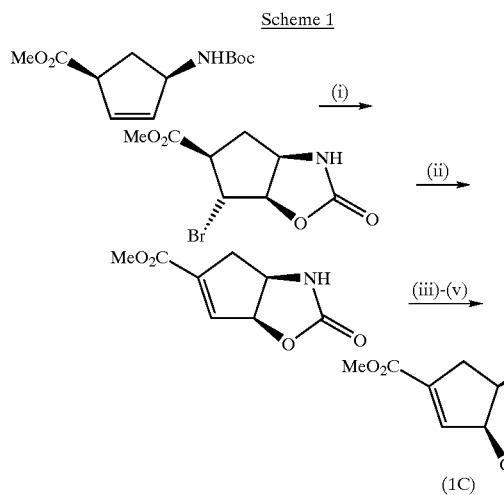

Step (i) is the preparation of a brominated bicyclic carbamate. This is achieved by treatment with N-bromosuccinimide (NBS) in a mixture of tetrahydrofuran and water. It is surprising that this reaction proceeds in high yield, since the same reagents are commonly used to convert an alkene to a bromhydrin (for example, see Adger et al, *J. Chem. Soc., Chem. Commun.*, 1999, 1713). Step (ii) is elimination of HBr, effected by treatment with 1,8-diazabicyclo[5.4.0]undec-7-ene (DBU). This gives an unsaturated bicyclic carbamate of formula (2). Steps (iii)–(iv) are sequential hydrolysis, protection of the amine is the N-Boc derivative, and re-esterification. This procedure affords a compound (1C) in a form suitable for further transformation, as detailed below.

A typical synthesis of a cyclopentene of formula (1B), e.g. the specific compound 1D) is shown in Scheme 2.

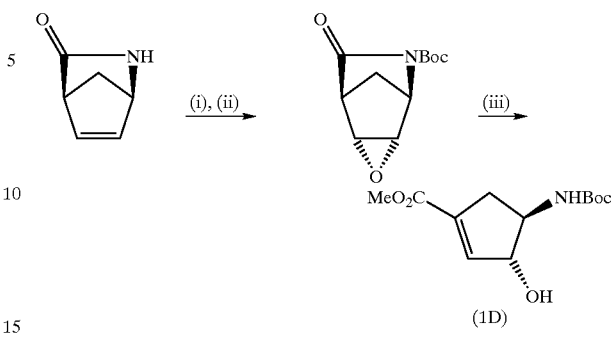

This synthesis commences from (−)-2-azabicyclo[2.2.1]hept-5-en-3-one and an identical sequence can be carried out on the (+)-enantiomer. Step (i) is the expoxidation of the (−)-lactam. This may be achieved using Oxide as oxidant, based on a literature procedure (Legraverened et al., *J. Heterocyclic Chem.*, 1989, 26, 1881). Step (ii) is the N-Boc-protection of the lactam epoxide using a standard protocol. Step (iii) is an elegant and novel double transformation effected by treatment with catalytic sodium methoxide in methanol. The lactam is ring-operation to give an epoxide methyl ester transiently, before this intermediate rearranges under the basic conditions to give the allylic alcohol.

A preferred embodiment of the invention is the synthesis of single stereoisomers of 3-tert-butoxycarbonylamino-4-hydroxycyclopentanecarboxylic acid methyl ester (4a–d) from the (1S, 4R)-methyl ester (1C), as depicted in Scheme 3 Likewise, the corresponding (1S, 4S)-methyl ester gives rise to the opposite enantiomeric series of four compounds.

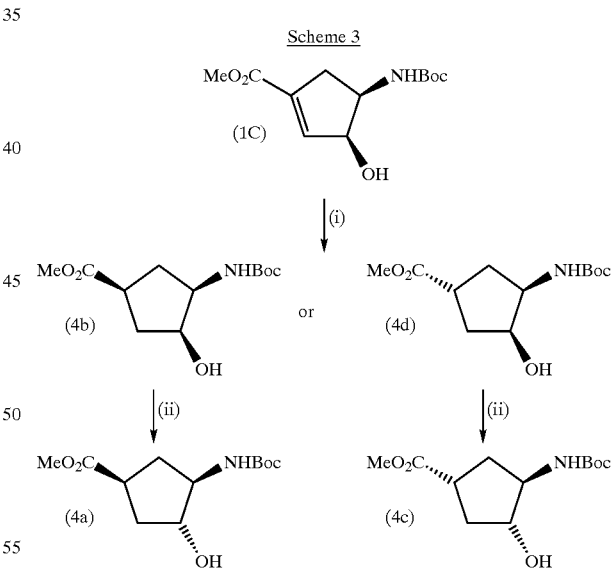

Step (i) is diastereoselective hydrogenation of the cyclopentene, for which complementary methods have been established. Using a conventional heterogenous catalyst such as palladium on carbon, hydrogen adds to the less hindered face of the substrate, to afford cycloalkane (4b) with all cis stereochemistry, as described in Example 6, infra. Conversely, a homogenous catalyst is required to effect addition of hydrogen to the more hindered face. Typically, such catalysts are transition metal complexes of phosphines, either chiral or achiral, capable of binding to a directing group also present in the hydrogenation substrate (for lead references, see Noyori, R., *Asymmetric Catalysis in Organic Synthesis*, John Wiley & Sons, Inc. Chapter 2, 1994; Ojima, I., *Catalytic Asymmetric Synthesis*, VCH Publishers (UK) Ltd., Chapter 1, 1993; Hoveyda et al, supra).

Without wishing to be bound by theory, it may be that the N-Boc functionality of (1C) serves as the primary catalyst-binding site. For the desired conversion of (1C) to (4d), several catalysts were screened and a surprising variation of diastereoselectivity was observed (Table 1). Judicious selection of catalyst is therefore required in order to obtain (4d) in acceptable isomeric purity, i.e of at least 60% de, preferably at least 80% de, and more preferably at least 95% de. For example, a suitable catalyst that has been found to fulfil this criterion is a rhodium complex of a DuPHOS ligand of formula (9), wherein R is $C_{1-10}$ linear alkyl. Other suitable catalysts can be found by experiment. As indicated in the first entry of Table 1, it is preferred that R is methyl, and additionally that the ligand is in the form of a single enantiomer.

TABLE 1 directed hydrogenation of (1a)

| catalyst | ratio of 4d:4b | diastereomeric excess (%) |
|---|---|---|
| [((R,R)-MeDUPHOS)Rh(COD)]BF$_4$ | 99:1 | 98 |
| [((R,R)-n-iPrDUPHOS)Ru](CF$_3$COO)$_2$ | 4:1 | 60 |
| [((R,R)-MeBPE)Rh(COD)]OTf | 39:1 | 95 |
| [((S,S)-MeBPE)Rh(COD)]OTf | 39:1 | 95 |
| [DiPFc-Rh(COD)]BF$_4$ | 2:1 | 33 |
| [((R,R)-n-iPrBPE)Ru](2-methyl allyl)$_2$ | 1:1 | 0 |
| [Ir(COD)Py(PCy$_3$)]PF$_6$ | No reaction (0–10 bar H$_2$) | — | abbreviations:
DUPHOS = 1,2-bis-phospholanobenzene.
BPE = 1,2-bis-phospholanoethane.
DiPFc = 1,1'-bis(diisopropylphosphino)ferrocene.
COD = Cyclooctadiene
PCy$_3$ = Tricyclohexylphosphine.
OTf = Trifluoromethanesulfonate.

Optional step (ii) in Scheme 3 is inversion of the 4-hydroxy function, for which conventional methods are applicable A typical protocol for step (ii) involves O-mesylation (MsCl/Et$_3$N), treatment with potassium acetate in DMF to effect nucleophilic substitution, and O-deacylation with sodium methoxide.

As indicated above, another aspect of the invention is the unexpected discovery that a compound of formula (1D) can be used to prepare either of the diastereomerically pure compounds represented by partial structures (4a) and (4c). Again, this may be followed by inversion to give cyclopentanes (4b) and (4d), respectively. The same methodology may be applied to the opposite enantiomers.

Scheme 4

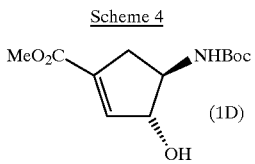

(1D)

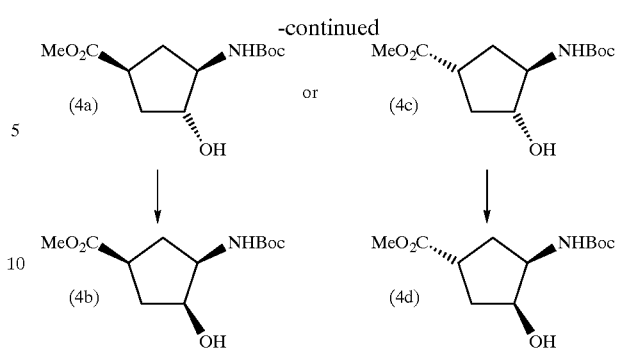

The conversion is achieved via a diastereoselective hydrogenation of the cyclopentene, for which complementary methods have been established. Several homogenous catalysts, based on transition metal-phosphine complexes, were screened. A variation in diastereoselectivity was observed (Table 2), but it is evident that conditions have been identified whereby the selectivity exceeded 60% and preferably 80% de (i.e. ratio of 4a:4c or ratio of 4c:4a is >9:1). Conditions giving <80% de are less preferred as preparative methods, since separation of the unwanted diastereosiomer becomes increasingly difficult and may reduce the yield of the desired isomer.

To access 4a as the major product, catalyst with the rhodium complex of DiPFc (Burk et al, *Tetrahedron Lett.*, 1994, 35, 4963) gives excellent diastereoselectivity (Table 2, entry 2), as does that with [Ir(COD)py(PCy$_3$)]PF$_6$ (Crabtree and Davis, *J. Am. Chem. Soc.*, 1986, 51, 26 and references therein) shown in entry 2. Conversely, to access 4c as the major product, rhodium complexes of phospholane ligands from the BPE(8) and DuPHOS (9) series can be used. Again, within these series of catalysts, judicious selection of ligand is required, but is readily achieved by the skilled person, in order to achieve sufficiently high diastereoselectivity, as is evident from entries 5–10. Preferred ligands are (R,R)-MeDuPHOS, (R,R)-MeBPE and (S,S)-MeBPE.

Without wishing to be bound by theory, it appears that, in process giving 4a, hydrogenation is directed by the hydroxyl group of the substrate, whereas in process giving 4c, direction by the N-Boc functionally on the opposite face of the ring is dominant. However, the factors that determine whether the hydroxyl group or the N-Boc functionality directs the hydrogenation are not obvious.

TABLE 2 directed hydrogenation of (1a)

| catalyst | ratio of 4a:4c | diastereomeric excess (%) |
|---|---|---|
| 1. [DiPFc-Rh(COD)]BF$_4$ | 32:1 | 94 |
| 2. [Ir(COD)py(PCy$_3$)]PF$_6$ | 32:1 | 94 |
| 3. {[(R,R)-4-Et-Fc]Rh(COD)}BF$_4$ | 6:1 | 72 |
| 4. {[(S,S)-4-Et-Fc]Rh(COD)}BF$_4$ | 3:2 | 20 |
| 5. {[(R,R)-MeDuPHOS]Rh(COD)}BF$_4$ | 1:23 | 92 |
| 6. {[(S,S)-MeDuPHOS]Rh(COD)}BF$_4$ | 1:2 | 33 |
| 7. {[(R,R)-EtDuPHOS]Rh(COD)}BF$_4$ | 1:7 | 75 |
| 8. {[(S,S)-EtDuPHOS]Rh(COD)}BF$_4$ | 1:2 | 33 |
| 9. {[(R,R)-MeBPE)Rh(COD)}OTf | 1:23 | 92 |
| 10. {[(S,S)-MeBPE)Rh(COD)}OTf | 1:34 | 94 |

Directed hydrogeneration can also be carried out when $R^5$ is H. An embodiment of this aspect of the invention is shown in Scheme 5.

Scheme 5

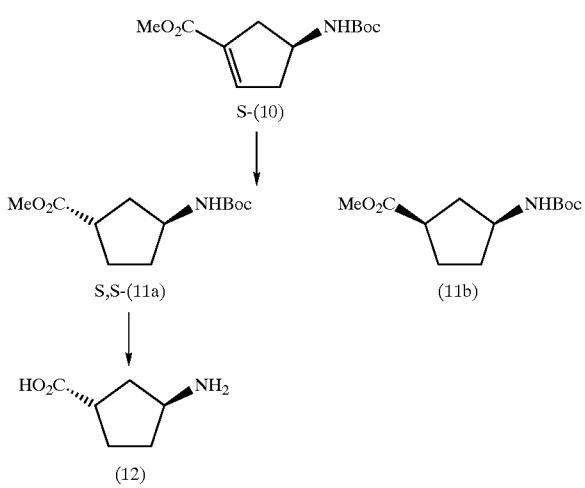

In this illustrative embodiment of the present invention, (1S,3S)-3-(tert-butoxycarbonylamino)-1-cyclopentanecarboxylic acid methyl ester [S,S-(11a)] is the major product in the hydrogenation of the cyclopentane S-(10). Likewise, in the opposite enantiomeric series, R,R-(11a) can be prepared from R-(10). The substrate S-(10) is prepared from (−)-2-azabicyclo[2.2.1]hept-5-en-3-one, which itself is obtained in an economically in an industrial bioresolution process (Taylor et al, *Tetrahedron: Asymmetry*, 1993, 4, 1117). Routine deprotection of the product S,S-(11a) gives the cyclic amino acid (12), belonging to a class of conformationally restricted GABA analogues for which useful biological activity has been demonstrated (Allan et al., *European J. Pharmacol*, 1986, 122, 139).

Table 3 summarizes the results observed in the hydrogenation of S-(10) with a range of catalysts Entry 1 shows the process of the present invention, wherein the ratio of S,S-(11a)] to the unwanted cis isomer (11b) is 96:4. For preparative purposes, this represents excellent stereocontrol, since this ratio is easily increased by recrystallization of the crude product mixture. In entries 2 and 3, catalysis with a Rh complex of a DuPHOS ligand also results in preferential formation of S,S-(11a), although stereoselectivity is markedly inferior. This degree of change is surprising since Me-BPE and Me-DuPHOS differ only the nature of the achiral backbone between phospholane units. In entry 4, employing the well established Ir(COD)py(PCy$_3$)]PF$_6$ complex, the unwanted cis-isomer is preferentially formed. Without wishing to be bound by theory, it may be that a simple steric effect is operating with this catalyst, such that hydrogenation occurs on the less hindered face of the cyclopentene ring. Entry 5 relates to the catalyst reported by Brown et al, supra. The results indicates that the conversion is unselective, with no directing effect.

Thus, it is evident from these results that carbamate derivatives of amines can act as effective directing group for hydrogenation of cyclic alkenes. The use of a Rh-BPE complex as catalyst is preferred, but other catalysts may be found by routine experiment.

TABLE 3 directed hydrogenation of S-(11a)

| catalyst | ratio of 11a:11b | diastereomeric excess (%) |
|---|---|---|
| 1 {[(R,R)-MeBPE)Rh(COD)}OTf | 24:1 | 92 |
| 2. {[(R,R)-MeDuPHOS]Rh(COD)}BF$_4$ | 4:1 | 60 |
| 3. {[(S,S-MeDuPHOS]Rh(COD)}BF$_4$ | 91:9 | 82 |
| 4 [Ir(COD)py(PCy$_3$)]PF$_6$ | 7.5:92.5 | 85 |
| 5 (1,4-Bis(diphenylphosphino)butane)(1,5-cyclooctadiene)Rh(I)BF$_4$ | 21.5:78.5 | 57 |

A preferred ligand (8) has a group R that is $C_{1-4}$ n-alkyl and preferably methyl or ethyl (respectively, methyl-BPE and ethyl-BPE). The ligand is used as a rhodium complex, typically as [Me/Et-BPE]Rh(COD))BF$_4$ Rhodium and ruthenium complexes, wherein the BPE ligand is present as a single enantiomer (R,R or S,S), are well established as effective catalyst for asymmetric hydrogenation of certain prochial substrates (for lead references, see Burk et al., *Pure Appl. Chem.*, 1996, 68, 37).

Overall, the present invention is based around a strategy of a divergent synthesis, as represented by Schemes 1 to 4. It is surprising that compounds (1) should serve as pivotal intermediates for trifunctionalised cyclopentanes, since their preparation entails removal of chiral information (see e.g. Scheme 1, step ii) which needs to be reintroduced (see e.g. Scheme 3, step i). For each enantiomeric series (as defined with respect to configuration of the nitrogen-bearing chiral centre), a single sequence of reactions provides a late-stage intermediate (1A) or 1B). This provides flexibility, since only 1 or 2 additional reactions are required in order to access a chosen chiral scaffold.

The invention thus provides a route to a series of scaffolds that can be used individually or as a library, for elaboration as desired. A recent illustration of utility is provided by the preparation of N-Boc-(e) and its methyl ester (4e) as a precursor of inactivators of GABA aminotransferase; see Qiu et al, *J. Med. Chem.* 2000, 43, 706.

The following Examples illustrate the invention (except where otherwise indicated).

EXAMPLE 1

(3aS,5R,6S,6aS)-6-Bromo-2-oxohexahydrocyclopentaoxazole-5-carboxylic acid methyl ester

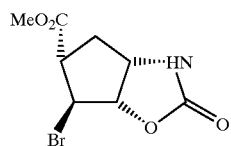

N-bromosuccinimide (164 g, 0.92 mol) was added in portions to a solution of (1R,4S)-4-tert-butoxycarbonylaminocyclopent-2-enecarboxylic acid methyl ester (200 g, 0.83 mol) in tetrahydrofuran (670 ml) and water (67 ml). The N-bromosuccinimide was seen to completely dissolve over 3 h period during which a mild exotherm was evident. The reactions was stirred for a further 14 h after which time it was concentrated to dryness under vacuum. The residue was redissolved in dichloromethane (11 L) and washed sequentially with 1M HCl (aq) (500 ml), saturated sodium sulfite (aq) (500 ml) and brine (500 ml) before driving over magnesium sulfate. Following filtration, concentration of the organic solution under vacuum yielded 238 g of a light brown solid. Recrystallisation from ethyl acetate/heptane yielded the title compound as white crystals (110 g, 50%). A further crop of crystals was obtained from the liquors although it was contaminated with a small amount of succinimide (49 g, 23%).

$^1$H-NMR (400 MHz, CDCl$_3$); δ2.42 (1H, dm, J14, 4-H), 2.52 (1H, dt, J 14 and 7, 4-H), 3.23 (1H, app quintet, J 7 and 3, 5-H), 3.75 (3H, s, CH$_3$), 4.43 (1H, app dt, J 7 and 2, 3a-H), 4.79 (1H, m, 6-H), 5.15 (1H, dd, J 7 and 2, 6a-H), 5.79 (1H, bs, 3-H).

EXAMPLE 2

(3aS,6aS)-2-Oxo-3,3a,4,6a-tetrahydro-2H-cyclopentaoxazole-5-carboxylic acid methyl ester

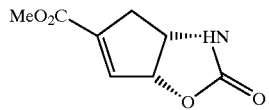

DUB (75 ml, 0.5 mol) was added dropwise to a cooled solution (5° C.) of (3aS,5R,6S,6aS)-6-bromo-2-oxohexahydrocyclopentaoxazole-5-carboxylic acid methyl ester (110 g, 0.42 mol) in dichloromethane (400 ml). A mild exotherm was observed. After a further 15 mins reaction was complete. The reaction mixture was washed with 1 M HCl (aq) (2×150 ml), the aqueous washings back-extracted with dichlormethane (3×100 ml) and the combined organic extracts dried over magnesium sulfate. Following filtration, concentration of the organic solution gave the title compound as an off-white solid (75 g, 98%).

$^1$H-NMR (400 MHz, CDCl$_3$); δ2.72 (1H, app dq, J 17, 3 and 2, 4-H), 2.88 (1H, ddd, H 17, 6 and 1, 4-H), 3.79 (3H, s, CH$_3$), 4.54 (1H, 3a-H), 5.62 (1H, m, 6a-H), 6.36 (1H, bs, 3-H), 6.66 (1H, app q, J 4 and 2, 6-H).

EXAMPLE 3

(3R,4S)-4-tert-Butoxycarbonylamino-3-hydroxycyclopent-1-enecarboxylic acid

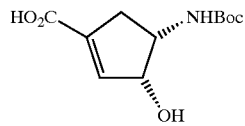

Potassium hydroxide (43 g, 0.76 mol) in water (150 ml) was added to a solution of (3a,6aS)-2-oxo-3,3a,4,6a-tetrahydro-2H-cyclopentaoxazole-5-carboxylic acid methyl ester (36 g, 0.19 mol) in methanol (150 ml). The mixture was heated under reflux at 90° C. for 2 days and allowed to cool. Methanol was removed under vacuum, the mixture diluted with water (100 ml) and the pH of the reaction was adjusted to pH 10.5 on addition of 1 M HCl (aq). The solution was cooled to 10° C. and a solution of di-tert-butyl dicarbonate (42 g, 0.19 mmol) in tetrahydrofuran (60 ml) was added dropwise and the mixture allowed to warm to room temperature. The reaction was then stirred for 14 h, the layer of tetrahydrofuran removed and the aqueous solution adjusted to pH 3 with 6M HCl (aq). The acidic solution was extracted with ethyl acetate (3×200 ml) and the combined organic washings dried over magnesium sulfate. Filtration then concentration under vacuum gave the title compound as a white solid (40 g, 86%).

$^1$H NMR (400 MHz, d6-DMSO), δ1.46 (9H, s, CH$_3$), 2.41 (1H, ddt, J 16, 6 and 1, 5-H), 2.65 (1H, app dd, J 16 and 7, 5 H), 3.41 (1H, bs, OH), 4.05 (1H, m, 4-H), 4.57 (1H, m, 3H), 6.40 (1H, d, J 7, NH), 6.58 (1H, m, 2-H).

EXAMPLE 4

(3R,4S)-4-tert-Butoxycarbonylamino-3-hydroxycyclopent-1-enecarboxylic acid methyl ester

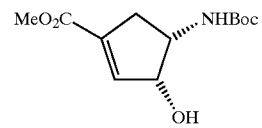

Methyl chloroformate (29 /ml, 0.37 mol) was added dropwise to a cooled solution (0° C.) of (3R,4S)-4-tert-butoxycarbonylamino-3-hydroxycyclopent-1-enecarboxylic acid (83 g, 0.34 mol) and triethylamine (52 ml, 0.37 mol) in methanol (600 ml). The reaction was stirred for 1 h at 0° C. and then allowed to warm to room temperature. After stirring for 14 h, it was apparent that the reaction was incomplete. After cooling to 0° C., triethylamine (30 ml, 0.22 mol) was added, and then methyl chloroformate (15 ml, 0.19 mol) was added dropwise. The reaction was complete after a further 2 h. The reaction mixture was concentrated under vacuum and the residue redissolved in dichloromethane (400 ml). The organic solution was washed sequentially with 1M potassium hydrogen sulfate (aq) (2×200 ml), saturated hydrogen carbonate (2×200 ml) and brine (200 ml) before drying over magnesium sulfate. Following filtration, the solvent was removed to yield an orange oil which was redissolved in methanol (300 ml) and cooled to 5° C. Sodium methoxide (0.25 ml, 25% wt solution in methanol, 3 mol %) was then added and the reaction mixture cooled and stirred for 4 h. The reaction was quenched with glacial acetic acid and concentrated under vacuum, and the residue was redissolved in dichlormethane (300 ml). The organic solution was washed with saturated sodium hydrogen carbonate (100 ml) then brine (100 ml) and dried over magnesium sulfate. Following filtration, the solvent was removed under vacuum to yield the title compound as an orange oil (76 g, 87%).

$^1$H-NMR (400 MHz, CDCl$_2$), δ1.46 (9H, s, CH$_3$ Boc), 2.50 (1H, m, 5-H), 2.92 (1H, dd, J 17 and 7, 5-H), 3.04 (1H, bs, OH), 3.77 (3H, s, CH$_3$ ester), 4.25 (1H, bs, 4-H), 4.77 (1H, bs, 3-H), 5.26 (1H, d, J 7, NH), 6.71 (1H, m, 2-H).

EXAMPLE 5

(1R,3R,4S)-3-tert-Butoxycarbonylamino-4-hydroxycyclopentanecarboxylic acid methyl ester

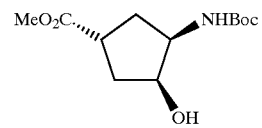

[(1,2-Bis(2R,5R)-2,5-dimethylphospholano)benzene](cyclooctadiene)rhodium(I) tetrafluoroborate (23 mg, 1 mol %) was added to a degassed solution of (3S,4R)-4-tertbutoxycarbonylamino-3-hydroxycyclopent-1-enecarboxylic acid methyl ester (1 g, 3.9 mmol) in methanol (5 ml). The reaction mixture was transferred to a bomb and, after purging with nitrogen and then hydrogen, a hydrogen pressure of 5 bar was applied and the reaction stirred for 14 h. The pressure was released and the bomb purged with nitrogen. Concentration of the reaction mixture gave a residue which was redissolved in dichloromethane (5 ml) Addition of silica (0.5 g) was stirring removed the catalyst from the reaction, and filtration and concentration of the organic solution gave the title compound as an off-white solid of 98% d.e. in quantitative yield.

$^1$H-NMR (400 MHz, CDCl$_3$); δ1.43 (9H, s, CH$_3$ Boc), 1.85 (1H, dt, J 13 and 10, 2-H), 2.05 (2H, m, 5-H), 2.26 (1H, m, 2-H), 3.10 (1H, m, 1-H), 3.67 (3H, s, CH$_3$ ester), 3.99 (1H, bs, 3-H), 4.27 (1H, m, 4-H), 4.91 (1H, d, J 7 NH)

EXAMPLE 6

(1S,3R,4S)-3-tert-Butoxycarbonylamino-4-hydroxycyclopentanecarboxylic acid methyl ester

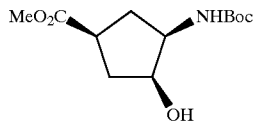

Palladium-on-carbon (1 g, 10 wt %) was added under nitrogen to a solution of (3S,4R)-4-tert-butoxycarbonylamino-3-hydroxycyclopent-1-enecarboxylic acid methyl ester (70 g, 0.29 mol) in methanol (300 ml). The reaction mixture was transferred to a bomb, and, after purging with nitrogen and then hydrogen, a hydrogen pressure of 2 bar was applied and the reaction stirred for 14 h (periodically, additional hydrogen was added to the reaction, to reestablish and initial reaction pressure). The pressure was released and the bomb purged with nitrogen. The reaction mixture was cautiously filtered through Celite® and then concentrated to give the title compound as a syrup of 90% d.e. in quantitative yield.

$^1$H-NMR (400 MHz, CDCl$_3$), δ1.42 (9H, s, CH$_3$ Boc), 1.74 (1H, app dq, J 17,2-H), 1.98 (1H, app dq, J 14, 5-H), 2.12 (1H, app heptet, J 14, 5-H), 2.39 (1H, app dq, J 17, 2-H), 2.91 (2H, m, 1-H and OH), 3.71 (3H, s, CH$_3$ ester), 3.92 (1H, bs, 3-H), 4.09 (1H, m, 4-H), 5.17 (1H, bs, NH)

EXAMPLE 7

(1S,3R,4S)-3-tert-Butoxycarbonylamino-4-methanesulfonoxycyclopentanecarboxylic acid methyl ester

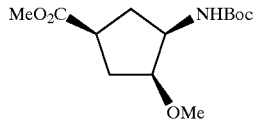

Methanesulfonyl chloride (17.0 ml, 0.22 mol) was added dropwise to a solution of (1S,3R,4S)-3-tert-butoxycarbonylamino-4-hydroxycyclopentanecarboxylic acid methyl ester (43.9 g, 0.18 mol), triethylamine (50 ml, 0.36 mol) and N,N-dimethylaminopyridine (1.1 g, 9 mmol) in dichloromethane (500 ml) at 0° C. After 45 minutes, the reaction was washed with 1 M citric acid (2×200 ml), saturated sodium hydrogen carbonate (200 ml), water (200 ml) and brine (100 ml), and then dried over magnesium sulfate. After filtration, concentration of the organic solution under vacuum gave the title compound as an off-white solid (55.6 g, 96%).

$^1$H-NMR (400 MHz, CDCl$_3$); δ1.44 (9H, s, CH$_3$ Boc), 1.91 (1H, m, 2-H), 2.32 (2H, m 2-H and 5-H), 2.44 (1H, app ddd, J 14, 5-H), 2.91 (1H, m, 1-H), 3.04 (3H, s, CH$_3$ mesylate), 3.71 (3H, s, CH$_3$ ester), 4.09 (1H, m, 3-H), 5.01 (2H, m, 4-H and NH).

EXAMPLE 8

(1S,3R,4R)-3-tert-Butoxycarbonylamino-4-hydroxycyclopentanecaboxylic acid methyl ester

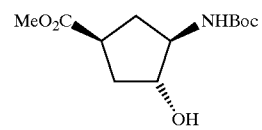

Potassium acetate (105 g, 1.05 mol) was suspended in a solution of (1S,3R,4S)-3-tert-butoxycarbonylamino-4-methanesulfonoxycyclopentanecarboxylic acid methyl ester (49.5 g, 0.15 mol) in dimethylformamide (250 ml). The stirred mixture was heated at 60° C. for 3 days cooled and diluted with dichloromethane (700 ml). The mixture was washed with water (1 L), saturated sodium hydrogen carbonate (500 ml), water (500 ml) and brine (300 ml) before drying over magnesium sulfate. Following filtration, concentration under vacuum gave the acetate as a brown solid which was recrystallized from tert-butyl methyl ether and hexanes. Sodium methoxide (0.7 ml, 25 wt % solution in methanol) was added to a solution of the recrystallised acetate (29.2 g, 0.10 mol) in methanol (300 ml) at 0° C. After 7 h, the reaction was quenched on addition of glacial acetic acid, and the solvent removed under vacuum. The residue was redissolved in dichloromethane (500 ml) and washed with water (200 ml), saturated sodium hydrogen carbonate (200 ml), water (100 ml) and brine (200 ml), before drying over magnesium sulfate. Following filtration, concentration under vacuum yielded a brown solid which was taken up in hot tert-butyl methyl ether (80 ml) and stirred with decolourising charcoal for 30 minutes. After filtration, heptane was added to yield the title compound as white crystal (18.6 g, 71%).

$^1$H-NMR (400 MHz, CDCl$_3$); δ1.44 (9H, s, CH$_3$ Boc), 1.71 (1H, app quintet, J 13 and 6, 2-H), 1.99 (1H, m, 5-H), 2.14 (1H, m, 5-H), 2.40 (1H, dt, J 13 and 8, 2-H), 3.07 (1H), 3.70 (3H, s, CH$_3$ ester), 3.79 (1H, bs, OH), 3.96 (1H, bs, 3-H), 4.13 (1H, m, 4-H), 5.26 (1H, d, J 5, NH).

EXAMPLE 9

Substrate Preparation (4S)-4-tert-butoxycarbonylaminocyclopent-1-enecarboxylic acid methyl ester

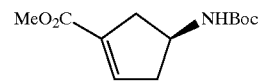

Sodium methoxide (8.23 ml of a 25% wt solution in methanol, 0.05 mol eq) was added dropwise to a stirred solution of (−)-N-Boc 2-azabicyclo[2.2.1]hept-5-en-3-one (150 g, 0.72 mol) in methanol (750 ml) at 0° C. After 30 minutes, the reaction was warmed to room temperature. After 60 h, the reaction was quenched with acetic acid and concentrated to dryness. The residue was redissolved in dichloromethane (700 ml) and washed with water (300 ml), saturated sodium hydrogen carbonate (300 ml) and brine (300 ml). The combined aqueous washings were then back extracted with dichloromethane (300 ml), the organic extracts combined and dried over magnesium sulfate. Filtration and concentration under reduced pressure gave a white solid which was recrystallized from ethyl acetate/heptane to give the title compound as white crystals (130 g, 75%)

$^1$H-NMR (400 MHz, CDCl$_3$); δ1.44 (9H, s, CH$_3$ Boc), 2.32–2.49 (2H, m, 3-H), 2.85–3.01 (2H, m, 5-H), 3.74 (3H, s, CH$_3$ ester), 4.36 (1H, app bs, 4-H), 4.74 (1H, app bs, NH), 6.69–6.75 (1H, m, 2-H).

EXAMPLE 10

Directed Hydrogenation (1S,3S)-3-tert-Butoxycarbonylaminocyclopentanecarboxylic acid methyl ester

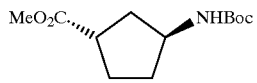

((1,2-Bis(2R,5R)-2,5-dimethylphospholano)ethane)(cyclooctadiene)rhodium(I) trifluoromethanesulfonate (179 mg, 0.1 mol %) was added to a degassed solution of (4S)-4-tert-butoxycarbonylaminocyclopent-1-enecarboxylic acid methyl ester (70 g, 0.29 mol) in methanol (350 ml). The reaction mixture was transferred to a bomb and after purging with nitrogen and then hydrogen, a hydrogen pressure of 5 bar was applied and the reaction stirred for 62 h. The pressure was released and the bomb purged with nitrogen. Concentration of the reaction mixture gave a residue which was redissolved in dichloromethane (300 ml). Addition of silica (20 g) with stirring removed the catalyst from the reaction and filtration and concentration of the organic solution gave crude product as a yellow oil that solidified on standing (92% d.e.; measured by gc analysis). Crystallisation from tert-butylmethylether and heptane gave the title compound as colourless needles of 97% d.e. (63 g, 89%).

$^1$H-NMR (400 MHz, CDCl$_3$); δ1.42–1.50 (10H, m, CH$_3$Boc and 4-H),1.72–1.90 (2H, m, 4-H and 5-H), 1.96–2.24 (3H, m, 2-H and 5-H), 2.90 (1H, app quintet, J8, 1-H), 3.67 (3H, s, CH$_3$ ester), 4.06 (1H, bs, 3-H), 4.55 (1H, bs, NH).

EXAMPLE 11

Comparative Hydrogenation (1R,3S)-3-tert-Butoxycaronylaminocyclopentanecarboxylic acid methyl ester

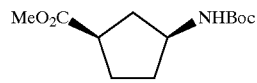

Tricyclohexylphosphine)(1,5-cyclooctadiene)(pyridine)iridium(I) hexaflourophosphate (1 mol %) was added to a degassed solution of (4S)-4-tert-butoxycarbonylaminocyclopent-1-enecarboxylic acid methyl ester (200 mg, 0.83 mmol) in methanol (4 ml). The reaction mixture was transferred to a bomb and after purging with nitrogen and then hydrogen, a hydrogen pressure of 5 bar was applied and the reaction stirring for 24 h. The pressure was released and the bomb purged with nitrogen. Concentration of the reaction mixture gave a residue which was redissolved in dichloromethane (5 ml). Addition of silica (1 g) with stirring removed the catalyst from the reaction and filtration and concentration of the organic solution gave the crude product as an off-white solid. The product was shown by GC analysis to be the title compound (85% d.e.).

EXAMPLE 12

(−)-Lactam Epoxide

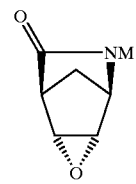

A solution of (−)-lactam (88 g, 0.81 mol) in 0.1 M sodium phosphate buffer (4L, pH 6) was cooled to 0° C. Oxone® (2 kg, 3.25 mol) was added over 5 h, during which time the pH was maintained at 6 by addition of 12 M NaOH (aq). After stirring for a further 2 h, mixture was filtered and the aqueous washed with dichloromethane (5 L). After drying over magnesium sulfate, the organic solution was concentrated under reduced pressure to yield the title compound as a white solid (32.3 g, 33%).

$^1$H-NMR (400 MHz, CDCl$_3$); d 1.70 (1H, app d, J 9.5, 7-H), 1.87 (1H, dd, J 9.5 and 1.5, 7-H), 2.92 (1H, m, 4-H), 3.60 (1H, dd, J 3.5 and 1.5, 5-H), 3.71 (1H, app d, J 4, 6-H), 3.39 (1H, m, 1-H), 6.76 (1H, bs, NH).

EXAMPLE 13

N-Boc-(−)-Lactam Epoxide

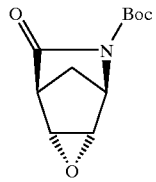

Di-tert-butyl dicarbonate (438 g, 1.76 mol) in dichloromethane (total volume of 600 ml) was added at room temperature to a stirred solution of (−)-lactam epoxide (200 g, 1.60 mmol), triethylamine (280 ml, 1.76 mmol) and 4-dimethylaminopyridine (cat.) in dichloromethane (750 ml) After 12 h, the mixture was washed with potassium hydrogen sulfate (0.3 M, 3×1 L) then brine (1×1 L) and dried. Following filtration concentration gave a brown solid that was recrystallised from acetate/hexanes. The brown crystals were harvested and redissolved in dichloromethane (2 volume equivs.) and silica (1 wt. equiv.) added to the stirred solution. After 15 minutes, the silica was filtered-off and the remaining solution concentrated to give the title compound as a white solid (245 g, 69%).

$^1$H-NMR (400 MHz, CDCl$_3$); 1.53 (9H, s, CH$_3$), 1.64 (1H, app d, J 10.5, 7-H), 1.81 (1H, app d, J 10.5, 7-H), 3.07 (1H, m, 4H), 3.62 (1H, dd, J 3.5 and 1.5, 5-H), 3.78 (1H, app d, J 4, 6-H), 4.63 (1H, m, 1-H).

EXAMPLE 14

(3R,4R)-4-tert-Butoxycarbonylamino-3-hydroxycyclopent-1-enecarboxylic acid methyl ester

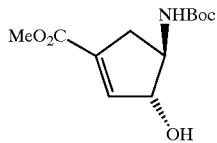

Sodium methoxide (50 mg, 4.5 mol %) was added to a solution a N-Boc-(−)-lactam epoxide (245 g, 1.09 mol) in methanol (1.85 L) at 0° C. After 1 h the reaction was warmed to room temperature and stirred for 14 h. The reaction was quenched with acetic acid and concentrated to dryness. The solid was redissolved in dichloromethane (1.5 L) and washed with sodium hydrogen carbonate (2×1L) then brine and dried. Following filtration, concentration under vacuum yielded exclusively the title compound as a white solid (250 g, 90%).

$^1$H-NMR (400 MHz, CDCl$_3$); δ1.46 (9H, s, CH$_3$ Boc), 2.32 (1H, qt, J 16, 8 and 2,5-H), 3.05 (1H, app dd, J 16 and 8, 5-H), 3.76 (3H, s, CH$_3$ ester), 3.96 (1H, m, 4-H), 4.39 (1H, bs, OH), 4.82 (1H, m, 3-H), 4.95 (1H, bs, NH), 6.65 (1H, bs, 2-H).

EXAMPLE 15

(1S,3R,4R)-3-tert-Butoxycarbonylamino-4-hydroxycyclopentanecarboxylic acid methyl ester

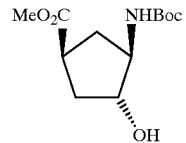

[1,1'-Bis(diisopropylphosphine)ferrocene] (cyclooctadiene)rhodium(I) tetrafluoroborate (56 mg, 0.1 mol %) was added to a degassed solution of allylic alcohol (20 g, 77.8 mmol) in methanol (150 mls). The reaction was transferred to a bomb and purged with nitrogen then hydrogen before establishing an initial reaction pressure of 2 bar. Pressure was maintained at 2 bar and the reaction stirred for 14 h. The pressure was released and the bomb purged with nitrogen. The reaction mixture was then concentrated under vacuum to give a solid that was redissolved in dichloromethane and treated with silica to remove the catalyst. After filtration, concentration under vacuum gave a solid that was recrystallised from methyl tert-butyl ether/hexane to give the title compound as white crystals of 95% d.e. (16.5 g, 82%).

$^1$H-NMR (400 MHz, CDCl$_3$); δ1.44 (9H, s, CH$_3$ Boc), 1.71 (1H, app quintet, J 13 and 6, 2-H), 1.99 (1H, m, 5-H), 2.14 (1H, m, 5-H), 2.40 (1H, dr, J 13 and 8, 2-H), 3.07 (1H, m, 1H), 3.70 (3H, s, CH$_3$ ester), 3.79 (1H, bs, OH), 3.96 (1H, bs, 3-H), 4.13 (1H, m, 4-H), 5.26 (1H, d, J 5, NH).

EXAMPLE 16

(1R,3R,4R)-3-tert-Butoxycarbonylamino-4-hydroxycyclopentanecarboxylic acid methyl ester

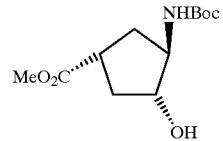

{[(1,2-Bis(2S,5S)-2,5-dimethylphosphate]ethane} (cyclooctadiene)rhodium(I) tetrafluoroborate (4.8 mg, 1 mol %) was added to a degassed solution of allylic alochol (200 mg, 0.77 mmol) in methanol (3 mls). The reaction was transferred to a bomb and purged with nitrogen then hydrogen before establishing an initial reaction pressure of 2 bar. Pressure was maintained at 2 bar and the reaction for 3 h. The pressure was released and the bomb purged with nitrogen. The reaction mixture was then concentrated under vacuum to give a solid that was redissolved in dichloromethane and treated with silica to remove the catalyst. After filtration, concentration under vacuum gave the title compound as a solid of 94% d.e. (16.5 g, 82%).

$^1$H-HMR (400 MHz, CDCl$_3$); δ1.44 (9H, s, CH$_3$ Boc), 1.68 (1H, m, 2-H), 1.90, dt, J 13.5 and 8, 5-H), 2.34 (1H, m, 2-H), 2.43 (1H, m, 5-H), 2.91 (1H, m, 1-H), 3.70 (3H, s, CH$_3$ ester), 3.78 (1H, m, 3-H), 4.01 (1H, m, 4H), 4.21 (1H, bs, OH), 4.75 (1H, d, J 3.5, NH).

What is claimed is:

1. A method of preparation of an isomerically pure compound having a structure as shown in (4a)–(4d):

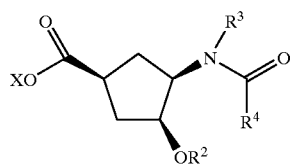
(4b)

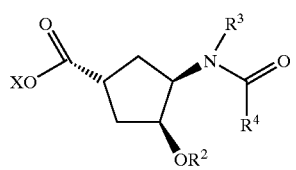
(4d)

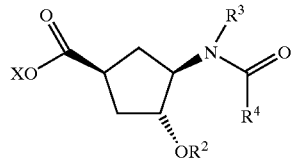
(4a)

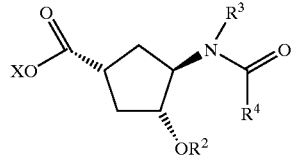
(4c)

or the opposite enantiomers thereof, wherein X is selected from the group consisting of alkyl, H, and a salt-forming cation, and $R^2$ is H or a protecting group;

$R^3$ is H or alkyl; and $R^4$ is selected from the group consisting of H, alkoxy, alkyl, aryl, and aralkyl; or, in the case of formula (1A), $R^2$ and $R^4$ are linked to form an oxazolidinone ring; and wherein said method comprises the use, in stereoselective hydrogenation, of a substituted cyclopentene compound, in substantially enantiopure form, having the relative stereochemistry according to formula (1A) or (1B)

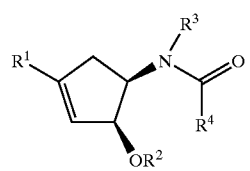
(1A)

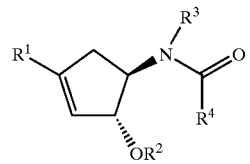
(1B)

including the opposite enantiomers, wherein
$R^1$ is either
COOX, wherein X is selected from the group consisting of alkyl, H, and a salt-forming cation, or $CH_2OH$, wherein the hydroxyl group is optionally protected;

$R^2$ is H or a protecting group;

$R^3$ is H or alkyl; and $R^4$ is selected from the group consisting of H, alkoxy, alkyl, aryl, and aralkyl; or, in the case of formula (1A), $R^2$ and $R^4$ are linked to form an oxazolidinone ring;

such that said isomerically pure compound having a structure as shown in (4a)–(4d) is produced by stereoselective hydrogenation of said substituted cyclopentene compound.

2. The method, according to claim 1, wherein said compound has a structure selected from the group consisting of:

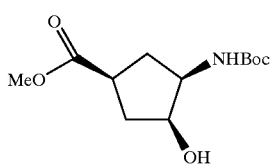
(4b)

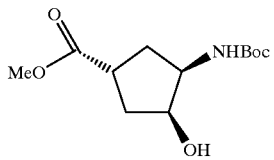
(4d)

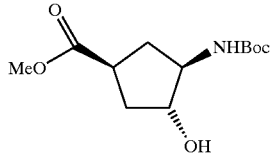
(4a)

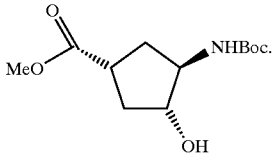
(4c)

3. The method, according to claim 1, which comprises hydrogenation of the methyl ester (1C):

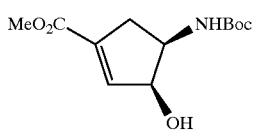
(1C)

4. The method, according to claim 3, to prepare compound (4b), wherein said hydrogenation is conducted in the presence of a palladium-on-carbon catalyst.

5. The method, according to claim 4, which additionally comprises inversion of the C-4 hydroxyl group to prepare compound (4a).

6. The method, according to claim 2, to prepare compound (4d), wherein hydrogenation is conducted in the presence of a rhodium complex of a diphosphine ligand of formula (8) or (9)

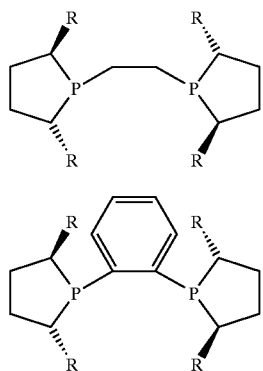

(8)

(9)

wherein R is $C_{1-10}$ linear alkyl.

7. The method, according to claim 6, wherein said ligand (9) is (R,R)-methyl-DuPHOS.

8. The method, according to claim 12, to prepare compound (4c), wherein hydrogenation is conducted in the presence of a rhodium complex of a diphosphine ligand of formula (8) or (9)

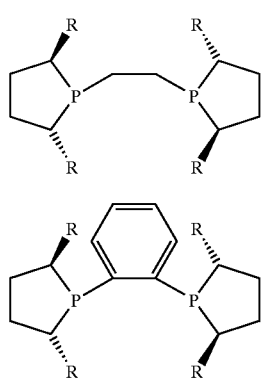

(8)

(9)

wherein R is $C_{1-10}$ linear alkyl; and wherein said ligand (9) is (R,R)-methyl-DuPHOS.

9. The method, according to claim 2, which comprises hydrogenation of the methyl ester (1D)

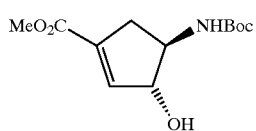

(1D)

or its opposite isomer.

10. The method, according to claim 9, to prepare compound (4a), wherein said hydrogenation is conducted in the presence of a catalyst selected from the group consisting of [DiPFc-Rh(COD)]BF$_4$ and [Ir(COD)py(PCy$_3$)]PF$_6$.

11. The method, according to claim 10, which additionally comprises inversion of the C-4 hydroxyl group to prepare compound (4b).

12. The method, according to claim 10, to prepare compound (4c), wherein said hydrogenation is conducted in the presence of, as catalyst, a rhodium complex of a ligand selected from the group consisting of methyl-DuPHOS and methyl-BPE.

13. The method, according to claim 12, wherein the cyclopentene (1D) has the absolute stereochemistry as depicted and the ligand is selected from the group consisting of (R,R)-methyl-DuPHOS, (S,S)-methyl-BPE, and (R,R)-methyl-BPE.

14. The method, according to claim 12, wherein the cyclopentene (1D) has the absolute stereochemistry opposite to that depicted and the ligand is selected from the group consisting of (S,S)-methyl-DuPHOS, (S,S)-methyl-BPE, and (R,R)-methyl-BPE.

15. The method, according to claim 12, which additionally comprises inversion of the C-4 hydroxyl group to prepare compound (4d).

16. The method, according to claim 8, wherein the cyclopentane (1D) is prepared from 2-azabicyclo[2.2.1]hept-5-en-3-one or any N-acyl derivative thereof.

17. The method, according to claim 16, commencing from 2-azabicyclo[2.2.1]hept-5-en-3-one, which comprises the following steps:

(i) treatment with an oxidant to effect stereoselective expoxidation on the less hindered face of the cyclopentene ring;

(ii) treatment with an acrylating agent to effect N-acylation; and (iii) treatment with an alcohol R$^1$OH and a base, to effect lactam ring-opening with concomitant formation of an ester and rearrangement of the epoxide group.

18. The method, according to claim 3, wherein the product of hydrogenation is formed in a diastereomeric excess of the least 80%.

19. The method, according to claim 18, wherein the diastereomeric excess is at least 90%.

20. A process for the preparation of a substituted cyclopentene of formula (5)

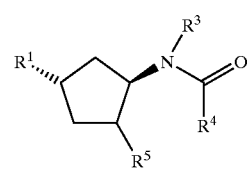

(5)

wherein

R$^1$ is either
COOX, wherein X is selected from the group consisting of alkyl, H, and a salt-forming cation, or
CH$_2$OH, wherein the hydroxyl group is optionally protected;

R$^2$ is H or a protecting group;

R$^3$ is H or alkyl;

R$^4$ is selected from the group consisting of H, alkoxy, alkyl, aryl, and aralkyl; or, in the case of formula 1A, R$^2$ and R$^4$ are linked to form an oxazolidinone ring; and R$^4$ is selected from the group consisting of H, α-OR$^2$, and β-OR$^2$, wherein said process comprises the stereoselective hydrogenation of an alkene precursor of formula (6)

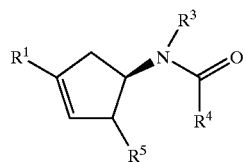

(6)

in the presence of a transition metal-phosphine ligand complex.

21. The process, according to claim 20, wherein the complex is cationic and the metal is rhodium.

22. The process, according to claim 20, wherein the ligand is of formula (8) or (9)

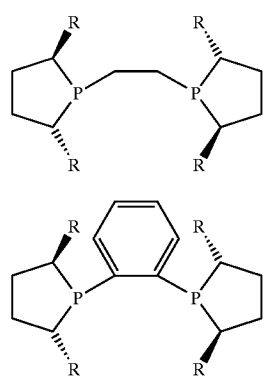

wherein R is $C_{1-10}$ linear alkyl.

23. The process, according to claim 20, wherein $R^5$ is $OR^2$.

24. The process, according to claim 20, wherein $R^5$ is H.

25. The process, according to claim 24, wherein the complex is of BPE ligand of formula (8)

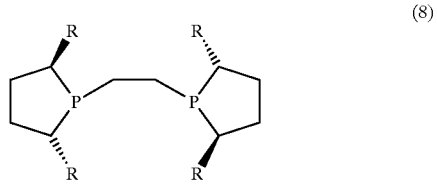

wherein R is $C_{1-6}$ n-alkyl, wherein the two P atoms are separated by an ethane bridge.

26. The process, according to claim 25, wherein R is methyl or ethyl.

27. The process, according to claim 25, wherein R is methyl.

28. The process, according to claim 24, wherein the product is butoxycarbonylamino-1-cyclopentanaecarboxylic acid methyl ester.

29. The process, according to claim 28, wherein the product is in enantiomerically enriched form.

30. The process, according to claim 20, wherein the product of hydrogenation is formed in a diastereomeric excess of at least 80%.

31. The process according to claim 20, wherein the product of hydrogenation is formed in a diastereomeric excess of at least 90%.

* * * * *